(12) United States Patent
Rappaport

(10) Patent No.: US 6,648,649 B2
(45) Date of Patent: *Nov. 18, 2003

(54) METHOD AND APPARATUS FOR ANALYSIS

(75) Inventor: Stephen A. Rappaport, Indianapolis, IN (US)

(73) Assignee: Agewell, P.C., Indianapolis, IN (US)

( * ) Notice: Subject to any disclaimer, the term of this patent is extended or adjusted under 35 U.S.C. 154(b) by 58 days.

This patent is subject to a terminal disclaimer.

(21) Appl. No.: 09/780,645

(22) Filed: Feb. 9, 2001

(65) Prior Publication Data

US 2001/0044099 A1 Nov. 22, 2001

Related U.S. Application Data

(63) Continuation-in-part of application No. 09/503,033, filed on Feb. 11, 2000, now Pat. No. 6,443,734.
(60) Provisional application No. 60/150,306, filed on Aug. 23, 1999.

(51) Int. Cl.[7] ............................................. G09B 19/00
(52) U.S. Cl. ..................... 434/236; 434/118; 600/300; 600/301; 705/2; 705/3
(58) Field of Search .................. 434/236, 238, 434/170, 118, 365; 707/5; 600/300; 345/1.1, 2.2, 719; 705/2, 3

(56) References Cited

U.S. PATENT DOCUMENTS

| | | |
|---|---|---|
| 1,326,695 A | 12/1919 | Schwarz |
| 1,516,097 A | 11/1924 | Hamilton |
| 1,683,827 A | 9/1928 | Ingram |
| 2,098,003 A | 11/1937 | Hassenfeld |
| 2,361,154 A | 10/1944 | Schoolfield |
| 2,414,614 A | 1/1947 | Shurick |
| 2,506,894 A | 5/1950 | Rowe |
| 2,511,953 A | 6/1950 | Tallman |
| 2,628,435 A | 2/1953 | Minninger et al. |
| 2,629,184 A | 2/1953 | Johnson |
| 2,816,380 A | 12/1957 | Sindell |
| 2,884,714 A | 5/1959 | Lawrence |
| 2,929,160 A | 3/1960 | Lyttle |
| 2,932,909 A | 4/1960 | Bosco |
| 3,382,590 A | 5/1968 | Mitchell |
| 4,326,711 A | 4/1982 | Giallombardo |
| 388,486 A | 8/1988 | Hall |
| 5,040,988 A | 8/1991 | Brown |
| 5,443,387 A | 8/1995 | Mortemard de Boisse |
| 5,696,981 A * | 12/1997 | Shovers .................... 704/10 X |
| 5,960,411 A | 9/1999 | Hartman et al. |
| 6,003,024 A | 12/1999 | Bair et al. |
| 6,029,141 A | 2/2000 | Bezos et al. |

(List continued on next page.)

Primary Examiner—S. Thomas Hughes
Assistant Examiner—Chanda Harris
(74) Attorney, Agent, or Firm—Doreen J. Gridley; Ice Miller

(57) ABSTRACT

An apparatus and method for analysis involving a first factor and a second factor. The first and second factors are related as expressed by a first relationship. The apparatus comprises a base divided into first, second and third sections, where the second section is positioned between the first and third sections. The first, second and third sections are representative of the first factor, the first relationship, and the second factor, respectively. The method of the present invention involves the steps of providing the apparatus and engaging in a dialogue of questions related to both the first and second factors. The apparatus and method of the present invention may be used in a variety of applications, such as biopsychosocial analysis, and analysis of the intellectual capital of a business, for example. The apparatus and method may be used for analysis involving more than two factors and presumes that some relationships exist between the factors. In one embodiment, an electronic representation of the apparatus and electronically converse with the user to lead to suggestions for treatments and/or changes needed to address the problem explained by use of the electronic system.

6 Claims, 6 Drawing Sheets

U.S. PATENT DOCUMENTS

| | | | | |
|---|---|---|---|---|
| 6,053,866 A | * | 4/2000 | McLeod | 600/300 X |
| 6,093,026 A | * | 7/2000 | Walker et al. | 434/322 X |
| 6,317,731 B1 | * | 11/2001 | Luciano | 706/21 X |
| 6,418,435 B1 | * | 7/2002 | Chase | 707/5 X |
| 6,422,558 B1 | * | 7/2002 | Chambers | 273/146 X |
| 6,425,764 B1 | * | 7/2002 | Lamson | 434/236 |
| 6,443,734 B1 | * | 9/2002 | Rappaport | 434/236 X |
| 2003/0055679 A1 | * | 3/2003 | Soll et al. | 705/2 X |

* cited by examiner

METHOD AND APPARATUS FOR ANALYSIS

RELATED APPLICATIONS

This is a non-provisional continuation-in-part patent application based on application Ser. No. 09/503,033, now U.S. Pat. No. 6,443,734 filed Feb. 11, 2000, which is based on provisional patent application Ser. No. 60/150,306, filed Aug. 23, 1999.

FIELD OF THE INVENTION

The present invention relates to a device and method for analysis involving at least two factors, with at least two of the factors related to each other.

BACKGROUND OF THE INVENTION

When multi-factor analysis of interrelated factors is attempted, the individual often has difficulty keeping track of which factors may have already been considered and what the relationship of those factors might be for a particular set of circumstances or facts. The same problem exists when two or more persons analyze such related factors, and may even be more complex and confusing depending on the role and contributions of those persons. Exemplary types of multi-factor analysis of related factors include, but are not limited to, those of biopsychosocial analysis and the analysis of the assets or capital of a business entity. Each of these examples is discussed in greater detail herein to assist in understanding the complexities associated with such analysis.

The dominant model of health care for health and illness is the "biomedical model", also referred to as the "medical model". This model is based on the assumption that illness results from physical causes, such as trauma or infection, for example. Therefore, psychosocial processes are not factors that cause disease under the biomedical model, as a person's illness or sickness must result from a disordered part of the body or from a pathological disease process. Problems with mood, emotion, thought or behavior are frequently categorized and analyzed as mental disorders or psychological disorders under the biomedical model.

Although there are limitations to the biomedical model, other models have had less widespread acceptance or use. The biopsychosocial model is one of those alternative models. The biopsychosocial model posits that health involves the interaction of biological psychological, and social/environmental factors in a person's life. In other words, health depends upon: (a) biological factors like structural defects (e.g., heart valve), weak function (e.g., inability to fight infection), or overactive function (e.g., allergy); (b) psychological factors including cognitive activities such as learning, remembering, analyzing, and emotional factors such as joy, anger, fear or sadness; and (c) social factors, including the closest social relationship (e.g., family) as well as reciprocal interactions with other individuals and institutions in the community.

Although the role of biological, psychological and social/environmental factors in health and disease is increasingly acknowledged, there is extreme lack of understanding about how these components interplay in wellness and illness. Such lack of understanding is due, in part, to the complex processes involved in analyzing linkages between personal, biological, psychological, and social/environmental data, and the increasingly limited contact time of a patient with health care professionals, including physicians. These problems may be expressed in other ways:

(a) Widespread physician beliefs and practices reinforce and perpetuate the overwhelmingly prevalent biomedical model. Consider, for example, the fact that very few physician-patient interactions include a balance of biomedical and psychosocial topics. Many such interactions do not result in an understanding of how these factors interplay or are used in effective, focused, joint decision-making. Physicians are more likely to perceive patients with psychosocial problems like depression or anxiety as "difficult"; such patients experience poorer functional status, unmet health expectations, reduced satisfaction, and greater use of health care services. Most patients are willing to confide psychosocial information to their physician, but rarely do unless a physician has previously expressed a specific interest. Thus, life events and social difficulties tend to merge indirectly as a part of a description of physical symptoms. Gynecologists are the de facto primary care physicians for many women, but a gynecologist's training emphasizes surgery, office procedures, infection, and metabolic disease treatment. Thus, such training provides little exposure to management of psychosocial problems. Referring patients with psychosocial problems to psychiatrists is inconvenient and expensive. For many patients with physical complaints, no organic cause can be found. One study showed that a psychiatrist evaluation and analysis improved subsequent treatment by the primary physician, but this also added greater complexity, cost, and inconvenience to the care process.

(b) The lack of biopsychosocial information leads to unnecessary suffering and expense. The most dramatic examples of this lack of information occur with syndromes such as chronic fatigue, chronic whiplash, repetition stress injury, and fibromyalgia. All these syndromes include a cycle in which a person connects continuing physical symptoms to an underlying serious disease. By thinking the problems will become worse and by expecting disability, a person can easily reinforce and perpetuate symptoms in a vicious cycle; assuming the "sick role" can prevent a person from ever getting well. Often stress remains an unresolved ongoing problem that affects an individual's well being and his or her ability to relate to others in a mutually beneficial manner.

(c) By not identifying and understanding the effect of life stressors, individuals confuse and confound the care process. The tendency in many instances to only address physical symptoms may lead people to cease seeking further medical advice if their needs are not met. Alternatively, an individual may frequently change physicians or see multiple physicians. These activities increase overall medical expenses, especially as people get older. Not understanding the biological, psychological, and social changes of an individual situation can increase distress and exacerbate the discomfort of chronic illness.

(d) Major health problems must have an integrated biopsychosocial approach for effective management and treatment. Such an integrated approach may be more expensive and is inherently more complex. The previously narrow biological paradigm of asthmatic disease is evolving in a way that gives scientific credibility to such an approach. The field of psychoneuroimmunology links psychosocial stress, the central nervous system, and changes in immune and endocrine function. This field describes biological paths by which stress affects respiratory function. Stress affects autonomic control of airways. Stressors such as living near a nuclear plant accident, being an Alzheimer's Disease caregiver, or taking difficult school exams have all been scientifically shown to affect the number and function of white blood cells. Stress triggers release of hormones that affect immune cells and increase susceptibility to viral respiratory infections. Management of asthma is a paradigmatic example of how the effects of family function, social support, thinking, personality, self-concept, stress, and coping ability are all important factors associated with favorable or unfavorable outcomes.

(e) Opportunities to improve one's physical condition are missed by not understanding one's psychological experience. People with even moderately severe asthma or rheumatoid arthritis who write about their stressful life experiences have significant clinical improvement. Depressive symptoms or lack of social support have been shown to affect cholesterol levels. Feelings of anger and hassle influence insulin and glucose metabolism in non-diabetic adults. Such findings occur not only in the United States, but throughout the world. Gastrointestinal diseases have exemplified the impact of psychological factors. Psychological factors impact diseases such as gastroesophageal reflux disease, chronic abdominal pain, Crohn's Disease, and Irritable Bowel Syndrome.

(f) Health professionals are not in a position to make the biopsychosocial model part of their practice. Such professionals continue to be trained using the biomedical model, and time pressures and constraints of their practices make evolution to a different model difficult. Use of the biomedical model results in a narrow view of the patient in terms of a disease to be diagnosed, treated, and cured, rather than as a person with an illness whose healing requires an understanding of the individual's personal situation. Treatment also requires collaboration between physician and patient.

(g) Without effective tools, use of a biopsychosocial model can be difficult to implement, excessively time consuming, or more expensive when compared to use of the biomedical model. Educators exhort physicians to be more empathetic, use opportunities for praise, learn moral reasoning, and develop a sense of duty. Physicians are advised to develop interviewing skills and not cut patients off in mid-sentence. Physicians are instructed to explore their feelings and raise their own level of awareness by avoiding burnout and attending support groups. Other resources recommended include educational videos, or written summaries of visits sent to the patient. None of these recommended techniques, skills, or resources have consistently had a measurable effect on health outcomes.

It is desired to develop a novel solution to the above problems—to provide a tool to allow people to discover personal biopsychosocial linkages prior to a professional encounter. Such a tool should be able to facilitate the physician-patient interactions by: (a) permitting patients and health professionals to recognize factors (such as anxiety, depression, illness beliefs, feelings about care) that perpetuate illness; and (b) allow patients to limit and control factors that precipitate illness by improving stress management skills, social support, and preventive health measures.

Despite the transformation in many industries from manufacturing to knowledge-based companies, most businesses have failed to maximize their total market value due to failure to develop their intellectual capital. Most businesses have recognized the value of traditional forms of capital such as financial capital and physical capital as well as the capital value inherent in the structure and processes of any organization. Many businesses have also recognized the capital value of certain human resources, for example, employee knowledge and skills.

But in today's business world, there is increasing recognition of an important "hidden value" of intellectual capital beyond the types of capital described above. Intellectual capital, among other things, consists of employee motivation and behavior, the organization's motivation and behavior, employee relationships, customer relationships, and the organization's relationships. Developing, applying, and leveraging these forms of intellectual capital are competitive areas of today's economy in which business market value depends increasingly on larger numbers of highly skilled employees.

Most businesses fail to recognize these hidden forms of intellectual capital because their organizational structure still reflects origins in Classical Management Theory that dates from the early part of the twentieth century. Based on mechanistic principles, Classical Management Theory put major emphasis on top-down command from management's centralized authority. In response, employees were expected to develop discipline and obedience. By de-emphasizing the thoughts, feelings, and interrelationships of workers, Classical Management Theory facilitated the assembly-line workplace common in many manufacturing, retail, and service industries. Over many years, this assembly line structure has naturally led to the replacement of skilled with unskilled workers. But in the current era, Classical Management Theory has become increasingly ineffective in maximizing the value of capital because of the transformation to knowledge-based industries with many skilled workers.

Most recent schools of management theory such as the Human Relations Movement (based on the work of Maslow et al.) and the Total Quality Movement (based on the work of Deming et al.) have reacted against the rigidity of Classical Management Theory. These schools have emphasized the importance of managerial style, informal group activities, and questioning operational norms, but they have had notable failures to integrate the 1) psychological and emotional reactions and 2) individual and group interrelationships in a way that directly improves productivity or increases the value of hidden intellectual capital. This failure has been due in part the lack of an easy-to-use tool to recognize, characterize, and analyze the interdependent structural, psychological and relationship-based aspects of an organization's hidden intellectual capital.

It is therefore desired to develop a novel solution to this problem by providing an analytic tool that allows the discovery of linkages between all different capital assets that comprise the overall market value of a company. Such a tool will help show the different forms of intellectual capital and how they can directly affect physical, financial, and structural capital of an organization. This tool will help in understanding and maximizing the interaction between different forms of capital in a way that enhances the overall market value of an enterprise.

In both the exemplary cases of biopsychosocial analysis and analysis of the capital of a business, the analysis is predicated on two or more related factors. In the case of biopsychosocial analysis, those factors are the social factors, biological or physical factors, and psychological factors. There is a relationship between the social and biological factors, between the psychological and biological factors, and between the social and psychological factors; for example, social factors may influence a person's physical well being, as may psychological factors. In the exemplary case of total capital analysis, those factors are 1) relationships including those between employees, customers, and organizations 2) motivation and behavior including those of customers, suppliers, employees and the organization and 3) other forms of capital of the organizations involved. There are relationships between #1 and #2, #1 and #3, and #2 and #3.

Self-help materials and tools have gained great popularity over the last several decades. People often seek ways to be introspective to solve their problems or to better equip themselves to ask questions of their health care providers. It is advantageous, however, if the person and the health care provider use the same materials and/or tools. Thus, it is desired to provide an analysis tool which can be used by the individual and the health care provider, either alone or in combination.

SUMMARY OF THE INVENTION

The present invention comprises an apparatus and method for analysis of a plurality of factors, some of which may be related to each other. In one embodiment of the apparatus of the present invention, the analysis involves a first factor and a second factor, with the first and second factors related to each other as expressed by a first relationship. The apparatus comprises a base divided into first, second, and third sections representative of the first factor, first relationship, and second factor, respectively. Each of the sections are further subdivided into a first subsection and a second subsection. The first subsection is indicative of a symptom, event, experience, problem, or causal relation, and the second subsection is indicative of a solution, treatment, needed change, or adjustment. The method of the present invention comprises use of such an apparatus and engaging in a dialogue involving a plurality of questions related to both the first and second factors. The dialogue may involve only one person or more than one person, and the questions are directed toward identifying the answers to each of the subsections of the sections of the base. The user(s) may use markers to keep track of the user(s)'s responses. Those markers may have words, symbols, or colors thereon, and may be made to match the shape of the subsections of the base.

In another embodiment of the present invention, the apparatus is comprised of five sections corresponding to three factors with one of the factors related to each of the other two factors. Each of the factors of analysis in this embodiment is subdivided into four subsections indicative of a: (1) symptom, event, experience, or problem; (2) causal relation; (3) solution or treatment; and (4) needed change or adjustment, respectively. In this manner the event, cause, solution, and adjustments for all three factors and for the relationships between the factors may be explored by the user(s) of the apparatus.

In one application of this embodiment, the analysis performed using the device is biopsychosocial analysis—evaluating biological, psychological, and social/environmental factors, with a biosocial relationship between the biological and the social/environmental factors, a biopsychological relationship between the biological and psychological factors, and a psychosocial relationship between the psychological and social/environmental factors. In this application, the individual (or an individual with his/her health care professional) can explore the biological, psychological, and social/environmental factors that may impact the individual's health.

In another application of this embodiment, the factors evaluated are relationships (those of employees, customers and the organizations), motivation and behavior (those of the employees and the organization), and other capital assets of an organization. The user of this application can evaluate the full range of the organization's assets, including its intangible assets such as intellectual capital.

In yet another application, the analysis tool of the present invention is presented in electronic form. The apparatus includes a processor, display terminal, user input mechanism and software. The software may reside on a personal computer, for example, or be accessible over a network, such as a global computer network known as the Internet.

DETAILED DESCRIPTION OF THE INVENTION

Figure 1:
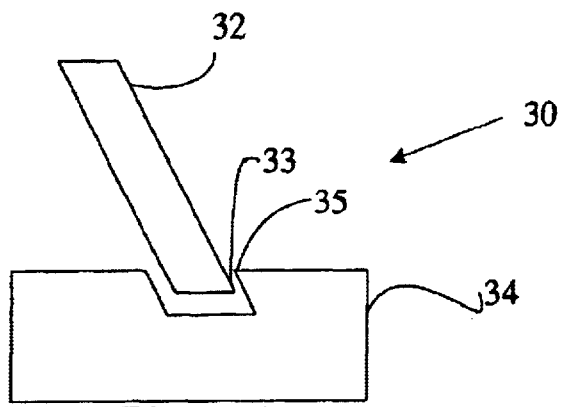
FIG. 1 shows a side view of one embodiment of the apparatus according to the present invention.
Figure 2:
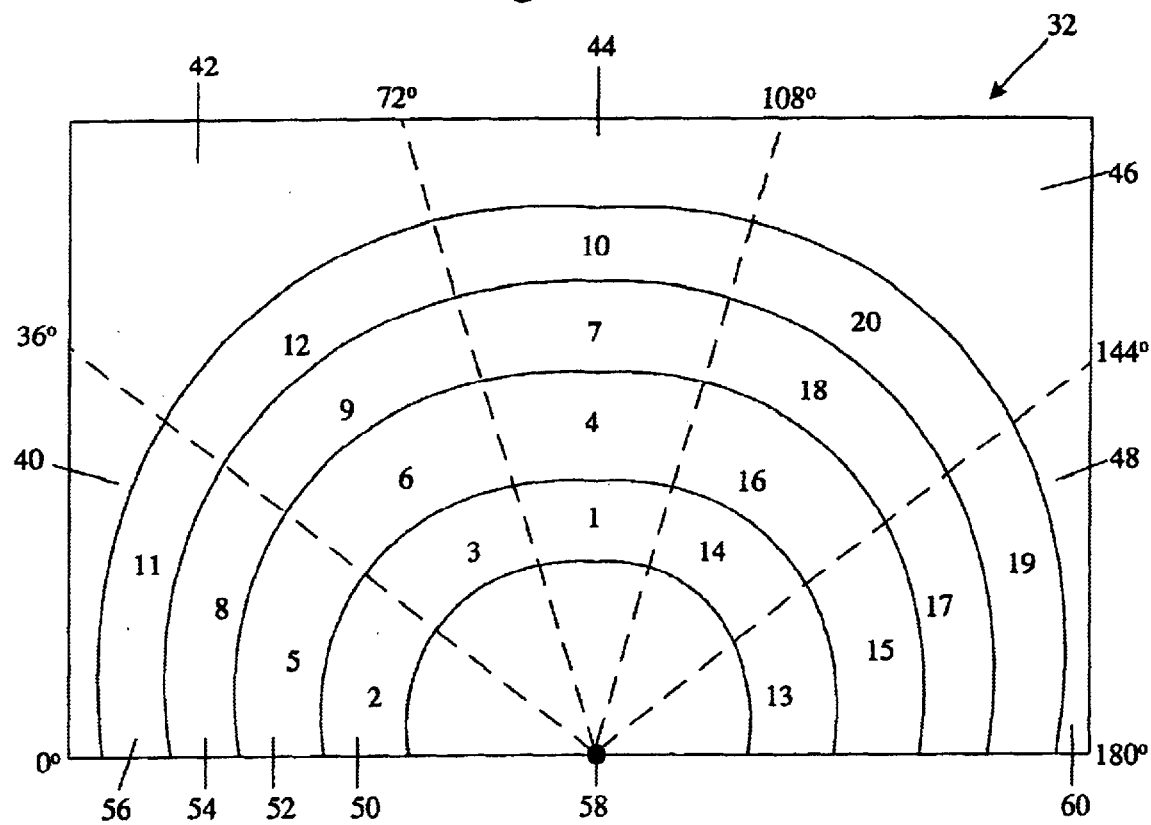
FIG. 2 shows a front view of the apparatus of FIG. 2.

The present invention comprises an apparatus and method for analysis involving a plurality of interrelated factors. The apparatus allows the user to construct color-coded words, symbols, and pictures to characterize the relationships between the factor analyzed. Referring now to FIGS. 1 and 2, there are shown a side view and front view of one embodiment of the apparatus of the present invention. In this embodiment, apparatus 30 comprises base 32 and block 34. Base 32 is a substantially flat wooden or plastic board as is shown in greater detail in FIG. 2. Block 34 serves as a means for supporting base 32 and, in this embodiment, comprises a wooden or plastic block having recess 35 therein to allow base 32 to be supported at various desired angles up to 90°. Base 32 is approximately 12 inches tall and 24 inches wide, and has grooved linear edge 33 at the bottom thereof to hold paper or plastic material thereon.

Base 32 is shown in greater detail in FIG. 2. In this embodiment, base 32 is divided into first section 40, second section 42, third section 44, fourth section 46, and fifth section 48. Base 32 is further subdivided into first, second, third, and fourth semicircular concentric rings 50, 52, 54, and 56, respectively, all centered about reference point 58 of substantially linear edge 60 of the perimeter of base 32.

Sections 40, 42, 44, 46 and 48 are each defined by lines originating from base reference point 58. First section 40 begins at zero degrees relative to linear edge 60 and continues through 36°. Second section 42, third section 44, fourth section 46, and fifth section 48 are also 36° in width, thus being of equal radial width with each other and with first section 40.

Sections 40, 42, 44, 46, and 48 and rings 50, 52, 54, and 56 may be imprinted directly onto base 32 or may be comprised of paper or plastic laid onto base 32 or adhered, by means well known in the art, either permanently or removably to base 32.

The combination of sections 40, 42, 44, 46, and 48 and rings 50, 52, 54, and 56 results in the division of base 32 into spaces 1 through 20 as illustrated in FIG. 20. The meaning of the spaces in various applications of the apparatus and method of the present invention is explained in greater detail herein.

Figure 3:
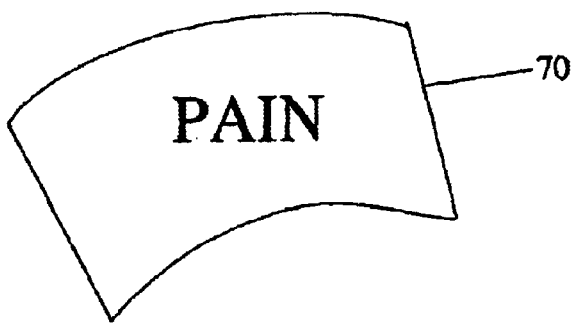
FIG. 3 shows a front view of one embodiment of a marker used with the embodiment of FIGS. 1 and 2.

To identify responses to questions in the method of the present invention, markers, such as that illustrate in FIG. 3 may be used. FIG. 3 shows a front view of marker 70 sized for placement over space 1 of the base 32. Marker 70 contains the word "PAIN" which is indicative of one of many possible responses to an inquiry related to space 1. The invention may comprise a plurality of markers for each of the spaces of base 32, and may be color coded, and/or have words, pictures, or symbols (such as drawings or the international symbols) thereon.

In one alternative, to begin the method of use of the apparatus of the present invention, consider base 32 as comprised of paper or plastic apparatus approximately 12 inches high and 24 inches wide is placed on grooved ledge 35. The front of base 32 has adhesive paper or plastic covering in the semicircular pattern defined by rings 50, 52, 54, and 56. The adhesive paper or plastic covering is cut into 20 contiguous pieces as shown in FIG. 2.

During use, in response to a question asked related to space 1, the adhesive portion under space 1 is removed to reveal space 1. The user marks space 1 with words, symbols, and/or pictures with a designated marker or with a red marker comprising an adhesive piece (paper or plastic) for adhesion to space 1. The significance of each of the spaces is discussed in greater detail herein in connection with the use of the invention. Likewise, in response to a question related to space 2, the adhesive portion under space 2 is removed by the user revealing yellow space 2. The user marks space 2 with words, symbols, and/or pictures with a designated marker or with yellow supplied marker for adhesion to space 2. A similar process is followed for space 3 (orange), and for spaces 4, 5, 6, 7, 8, 9, 10, 11, and 12. In this embodiment, all spaces between 0 to 36 degrees are colored in yellow, all spaces between 36 to 72 degrees are colored in orange, all spaces between 72 and 108 degrees are colored in red, all spaces between 108 and 144 degrees are purple, and the spaces between 144 and 180 degrees are blue.

When many or all of the spaces have been revealed and marked, the apparatus has been used to create a color-coded paper or plastic hemiannular device. The hemiannular device may be removed from block 34 and covered with iridescent or clear plastic coating or film. The removed and covered device may then be attached to an adhesive pop-up tab in a paper or plastic folder that opens to display it in a three-dimensional manner. The result is a three-dimensional fold-out base, which the user has marked with words, symbols, pictures, and/or colors based on responses to questions.

One application of the apparatus and method is in biopsychosocial analysis. In this application, sections 40, 42, 44, 46, and 48 (pie-slices in shape) relate to:

| Angle of Slice | Factors |
| --- | --- |
| 0–36 | Social/Environmental |
| 36–72 | Biosocial Linkages (Relationships) |
| 72–108 | Biological/Physical |
| 108–144 | Biopsychological Linkages (Relationships) |
| 144–180 | Psychological |

In other words, first section 40 is representative of the first factor, the social factor or social/environmental factor of the analysis. Third section 44 represents the biological/physical factor of the analysis and fifth section 48 represents the psychological factor of the analysis. Second section 42 represents the relationship between the first and second factor of the analysis, and fourth section 46 represents the relationship between the second and third factors of the analysis.

Rings 50, 52, 54, and 56 relate to:

| Ring | Spaces in Ring | Treatment Indicators |
| --- | --- | --- |
| 1 | 2, 3, 1, 14, 13 | Symptom, event or experience |
| 2 | 5, 6, 4, 16, 15 | Causal Relation |
| 3 | 8, 9, 7, 18, 17 | Solution or Treatment |
| 4 | 11, 12, 10, 20, 19 | Change or Adjustment Needed |

A qualified individual or proctor can, based on these factors and treatment indicators, complete various aspects of biopsychological analysis of the individual to assist the health care professional in diagnosis and treatment of the individual. The method of analysis of the present invention is presented herein by way of Examples 1, 2, 3, 4, 5, 6, and 7.

EXAMPLE 1

Consider a patient who has urinary incontinence and who comes to an urologist for medical treatment. Before seeing the urologist, the patent will sit down with a proctor. This proctor is an individual trained in the use of the device of the present invention and may be a nurse, physician assistant, or a physician. Although there is no dictated order to the questions asked (and thus spaces completed), an example of a dialogue between the patient and the proctor and use of the device is as follows:

Proctor: Why are you here to see the doctor? (Seeking an answer relative to space 1—physical symptom, event or experience)

Patient: I have urinary incontinence for which I have been using incontinence pads. I thought there might be something else I could do. (The patient places a word, symbol or picture in space 1 to be illustrative of the physical symptom)

Proctor: How does the problem make you feel? (Seeking an answer to space 13—psychological symptom, event or experience)

Patient: I feel lonely and ashamed. (The patient places a word, symbol or picture in space 13 indicative of her loneliness and shame)

Proctor: Let's explore why you might be incontinent. (The proctor asks a series of questions directed at space 4—the physical cause of her incontinence—and determines that it is likely due to the patient's multiple pregnancies)

Patient: (Completes space 4 with a word, symbol or picture indicative of her multiple pregnancies)

Proctor: Possible alternative treatments include medicine or muscle training by pelvic floor exercises. (Seeking to complete space 7—solution or treatment for incontinence)

Patient: (Completes space 7 with words, symbols or pictures indicative of the treatments.) How can I learn floor exercises? (This question is directed toward space 10—change or adjustment needed for one of the treatments)

Proctor: There are a variety of ways; let's explore a little to determine which way might best suit you. You said you felt lonely and ashamed. Do you have any ideas why you feel that way? (Seeking an answer to space 15—causal relation of psychological symptom.)

Patient: I can't play tennis like I used to do all the time. (Completes space 15 with word, symbol or picture indicative of desire to play tennis)

Proctor: Would the ultimate solution be one that permitted you to play tennis again? (Seeking an answer to space 17—solution for psychological symptom.)

Patient: Yes! (Completes space 17 with word, symbol or picture indicative of playing tennis)

Proctor: Would you like to join a group that would let you be involved in sports? (Seeking an answer to space 19 change or adjustment needed to relieve psychological symptom)

Patient: Yes that would be good. I'd like to be active again. (Completes space 19 with word, symbol or picture indicative of joining a group for sports)

Proctor: It seems that your loneliness and shame are directly attributable to the physical problem of urinary incontinence. (Establishing a link between the physical and psychological for space 14)

Patient: I guess it is. (Completes space 14 with word, symbol or picture indicative of this link)

Proctor: Further, the urinary incontinence is limiting your athletic activities. (Establishing a causal relationship between the physical and psychological for space 16)

Patient: Yes, and I'm tired of it. (Completes space 16 with word, symbol or picture indicative of the link)

Proctor: We've said that one solution, pelvic floor exercises, could get you back into sports. Would you like to try such exercises? (Seeking an answer to space 18—solution or treatment that meets both the physical and psychological needs of the patient)

Patient: Yes, I'd like to give it a try. (Completes space 18 with word, picture or symbol indicative of floor exercises)

Proctor: To join a group for sports, you'll need to learn the floor exercises. (Seeking an answer to space 20—change or adjustment needed to satisfy both physical and psychological needs)

Patient: I'm ready. When do I begin? (completes space 20 with word, picture or symbol indicative of learning exercises)

Through this session with the proctor, the patient has explained the physical and psychological aspects of her illness, and the biopsychological linkages therebetween. The patient can take the completed hemiannular device to the urologist for further discussion, leading to ultimate diagnosis and treatment of both her physical and psychological symptoms. The social environment could also be explored in a similar manner.

EXAMPLE 2

A patient comes to see a cardiologist for chest pain. The patient has already consulted a general internal medicine specialist and been through a battery of tests to eliminate the diagnosis of any indigestion or like problem. Because the patient insisted that something is wrong, the internist recommended that the patient seek the advice of a cardiologist. The patient is frustrated with the ongoing pain and therefore heeds the internist's advice.

After being called into the cardiologist's consultation room, the patient is greeted by a physician assistant who explains that they are first going to talk about the problems using a new device to document their discussion. That device is the device of the present invention. The conversation between the patient and proctor (physician assistant) proceeds as follows:

Proctor: Why are you here to see us today? (Seeking information for space 1—physical symptom, event or experience)

Patient: I have chest pain, which my physician has clearly identified as not caused by indigestion problems. My physician suggested I see a cardiologist. (Completes space 1 of device with word, symbol or picture illustrative of chest pain)

Proctor: Have there been any changes in work or in your leisure time lately? (Seeking information for space 2—social/environmental symptom, event or experience)

Patient: I'm having fewer meals with friends because my work schedule has been crazy. I've been eating more fast food lately as a result. (Completes word, symbol or picture in space 2 indicative of isolation)

Proctor: Why aren't you eating with friends when the work schedule permits? (Seeking information for space 3—biosocial link between physical and social/environmental symptoms)

Patient: I think I have a serious medical condition so I stay home when it causes problems. (Completes space 3)

Proctor: What symptoms are so troubling that you stay at home? (Seeking more information for space 1—physical symptoms)

Patient: My heart races and I get dizzy. Sometimes I'm so dizzy, I have to lie down for a while.

Proctor: Let's see the cardiologist. It sounds as though some tests might be appropriate.

(At this time, the session is suspended. The patient sees the cardiologist who subsequently prescribes a battery of tests and sets up a return visit. The tests indicate that the patient has a ventricular arrhythmia. When the patient returns to the physician's office, the patient and proctor resume discussion using the device.)

Proctor: As the doctor has already told you, we have identified the cause of your dizziness and chest pain—ventricular arrhythmia. What questions do you have about this condition?

Patient: The doctor was very clear about what ventricular arrhythmia is. (Completes space 4—causal relation of his symptoms)

Proctor: The most common treatments available are daily medication or one-time placement of a pacemaker. (Giving information for space 7)

Patient: (Completes space 7)

Proctor: The medicine must be taken every day. Inserting the pacemaker requires a surgical procedure.

Patient: (Completes space 10—change or adjustment needed for treatments)

Proctor: Has the pain affected your work? (Seeking information for space 5—causal relation of social/environmental symptoms)

Patient: I've been traveling less, and, as I told you before, staying home more. (Completes space 5)

Proctor: What is your goal for treatment? (Seeking information for space 8—solution for social/environmental aspects)

Patient: I want to get out more to spend time with friends. (Completes space 8).

Proctor: To accomplish that objective, you'll have to make more of an effort to plan social activities. (Seeking information for space 11—change or adjustment needed for social/environmental aspect)

Patient: I'm willing to do that. (Completes space 11)

Proctor: What else has stopped you from going out? (Seeking information for space 6—linkage for cause between social/environmental and physical)

Patient: I haven't been driving because of the dizziness. (Completes space 6)

Proctor: Would treating your heart problem help you to drive again? (Seeking information to space 9—linkage between social/environmental and physical as to treatment)

Patient: Yes, I'd love to do more driving again—I miss it. (Completes space 9)

Proctor: It seems clear that your choices are to take daily medicine or to have the surgical procedure so you can return to normal activity. Would you agree? (Seeking information for space 12—change or adjustment needed for both physical and social/environmental treatments)

Patient: I do agree. (Completes space 12)

Proctor: To help you decide, let's discuss the options in more detail with the cardiologist.

EXAMPLE 3

Consider a person whose disorganized control of personal affairs is unmasked by the new onset of cardiac problems. The person carries no health insurance but has hidden this fact from other family members. This is an example of a dialogue in which the device facilitates understanding and analysis of the biosocial aspects that affect the person's overall well being.

Proctor: What brings you here?

Patient: I started to experience chest pain this morning. There is a sharp pain in the center of my chest that radiates down my left arm. I never had pain like this before, so I came to have it evaluated. Space 1

Patient: But I want to tell you first that I have no healthcare insurance. I feel very guilty about this, but our household expenses were too great last year. To save money, I just let our insurance coverage lapse. We've been lucky that no medical problems have occurred since then, but now here is this new problem of chest pain. Space 2

Patient: I am really scared to tell my spouse about all of this. My spouse does not know that we have no health insurance coverage. Is there some way you can evaluate my chest pain using the least expensive tests possible? Space 3

(At this time, the interview is suspended for a period of time while tests are done. The patient and proctor reconvene later.)

Proctor: The results of the tests show that you have coronary artery disease, and your chest pain is angina pectoris. Angina occurs when your heart does not get enough blood flow and oxygen. Fortunately, there has been no permanent damage to your heart. Space 4

Patient: I have been leading a really sedentary lifestyle. I rarely exercise and eat a lot of high fat food. I was raised eating high fat food, so I never thought seriously about changing the habit. Space 5

Patient: This may not merely be a problem with my heart. Many things have combined to make my current situation difficult including my lifestyle, diet, and finances. I am also concerned about the consequences of deceiving my spouse about our health insurance. Space 6

Proctor: Your disease is fortunately not severe enough to require any special procedures or surgery to open up the blood vessels to your heart. You will only need to take a couple of medicines and to decrease fat and cholesterol in your diet. Space 7

Patient: Will I really need to change my whole daily routine? I have not been able to exercise much on my own, but perhaps I will find it easier to go work out with a friend. I dread sitting down to discuss family finances because my spouse will be shocked to learn that we do not have any health insurance because of what I have done. Space 8

Proctor: Do not see this diagnosis as the beginning of decline from disease. You have a new opportunity. This is a wake-up call to change your lifestyle in favor of better nutrition and exercise. It is also an opportunity to work cooperatively with your spouse to finally get the household affairs in order. Space 9

Patient: First, I need to learn more about angina pectoris and to maintain a daily routine. I will not forget to take the medicines at a regular time each day. I am going to report any side effects of the therapy to you. Space 10

Patient: My spouse has recently been interested in returning to work—hopefully to a job with health insurance benefits. We can start now to organize our finances and finally make a budget after all these years. Space 11 (Patient subsequently talks to spouse based on completion of Space 12 of the device)

Patient: It is hard for me to bring this up, but we need to talk about several things. I have recently found that I have a heart problem. I want to tell you about my treatment and about changes we can both make to lead healthier, more active lives. I also want to work with you to organize our finances for the future. Space 12

EXAMPLE 4

Consider a mother with vision and hearing problems that are difficult to treat because of her vanity and lack of insight. An adult daughter visits her mother's physician and with permission uses the device to understand how improving her mother's vision and hearing can occur only as part of a more comprehensive biosocial plan.

Daughter: My mother lives alone and sells cosmetics. Recently she is starting to have increasing trouble understanding what people around her are saying. She often ignores people standing on her right side. You have been treating my mother for high blood pressure, elevated cholesterol, and preventative therapy with estrogen post-menopause. Space 1

Daughter: The hearing problem is severe enough to affect her friendships and her livelihood. But my mother insists that nothing is wrong. If she continues doing this, I am concerned that she will lose her job and her friends. Space 2

Proctor: The problems you describe are primarily with your mother's work and her relationships with other people. During your mother's upcoming annual physical examination, let's complete some diagnostic testing to see what underlying medical problems may be contributing to the situation. Space 3

(At this time the interview is suspended for a period of time while the annual physical examination is completed. The proctor and daughter reconvene later).

Proctor: The results of the diagnostic evaluation show that she has a bilateral sensorineural hearing loss. Her hearing loss is most severe in the right ear. We also ordered a detailed eye exam, which shows that she has bilateral cataracts. Space 4

Daughter: Mother insists she is healthy and that she has a good memory, but she has little insight into how her vision and hearing problems are affecting her. I need to share this information with other family members so that at least they understand that these problems have been affecting the way my mother relates to them. Space 5

Proctor: You can see a more complete picture developing during our discussion. Your mother does not just have hearing loss and diminished vision. She has increasingly severe overall sensory loss. Problems with both vision and hearing magnify each other—sometimes disrupting a person's entire lifestyle and social circle. Space 6

Daughter: But we have already discussed these findings with my mother many times. She adamantly insists that a hearing aid is too expensive and too much trouble to maintain. She is afraid of having the cataract surgery to treat her vision problem. Space 7

Daughter: In this situation, our family members should work intensively to try to change mother's opinion and get her to cooperate with the treatment she needs. We will use the strength of our family relationships to impress how important these treatments are for her ongoing well being. Space 8

Proctor: Family members can certainly influence your mother's decisions about treatment. By offering to provide transportation, housekeeping, and meal preparation after she has the cataract surgery—they can help ease her fears about recuperating. Space 9

Daughter: The physician's office may be the most persuasive influence, so please stress to mother the safety of today's cataract operations. She may become more willing to have it done. Space 10

Daughter: Now that I understand these important problems, there is much I can do to help her obtain a hearing aid as well. For example, I can offer to take mother to learn more about hearing aid use and care. I can ask my own questions to the audiologist, and I will be able to reinforce any instructions mother receives. I can also schedule certain family members to come to her house after cataract surgery to help with errands, chores, and homemaking. Several of us also need to be with her the day of the surgery so that mother can get home safely and easily. Space 11

Daughter: If each family member coordinates efforts and gives mother the same message, we can help her out of "sensory deprivation" to a more active and fulfilling life. Space 12

EXAMPLE 5

Consider a person with insulin dependent diabetes mellitus. At first glance, the person seems to be experiencing progression of the disease. Use of the device reveals that these symptoms actually are due to biopsychological influences rather than progression of diabetes.

Proctor: What problems are you having?

Patient: Although I have lived with diabetes for many years, now I am experiencing more severe dry mouth and more frequent urination. I am also starting to have blurry vision and an upset stomach. Space 1

Proctor: Have other things happened to you since our last visit?

Patient: My increasing responsibilities at work have been very stressful. In fact, I would rate my stress level as 9 on a 10-point scale. Space 13

Proctor: There may be a link between some of the work-related problems you are experiencing and the elevated blood sugar levels. Space 14

Proctor: Problems with dry mouth, urinary frequency, and blurry vision are important to evaluate further. We'll order diagnostic tests to help determine the underlying cause of these symptoms. Your blood glucose self-monitoring levels were very high around the time of your last visit. Since then, I notice there has been a several week period when your blood glucose levels were normal. Space 4

Patient: My blood glucose levels were normal during the time I went on vacation. It was an active vacation with lots of hiking and swimming. I really had a chance to relax during that couple of weeks. Space 15

Proctor: There can be a link between high levels of stress and high blood sugar. All that physical activity may have had a relaxing effect that decreased your tension. Before vacation, you probably had become accustomed to using higher insulin doses than you later needed during the vacation period. Space 16

(At this time the interview is suspended for a period of time while tests are performed. The proctor and patient reconvene later.)

Proctor: We have evaluated to make sure that you have no underlying infection, no eye problems, or urinary diseases. These tests show that your diabetes is probably not progressing or increasing in severity. You do not need any more medication than you are already taking. Space 7

Patient: You explained that stress was causing the problems I experienced. I was able to control the stress during vacation. I should try to get away more frequently, but I cannot get away for vacation much more than I am now. Space 17

Proctor: You can certainly make an effort to decrease your stress level. For example, more regular exercise or use of specific relaxation techniques can be valuable. Doing this would not involve much more effort than you now use to monitor your blood glucose and regulate your insulin dose. Space 18

Since insulin therapy is now a regular part of your daily self-care program, the next step would be to make exercise and stress reduction techniques part of your daily health maintenance routine. Space 10

Patient: I am going to seek out an instructor who can teach me specific relaxation techniques—using visualization, deep breathing, and progressive muscle relaxation. I must learn to do these correctly if they are to be effective. Space 19

Patient: I am already starting to think about how to fit these in my daily work schedule. Perhaps I can use break periods to really decrease my stress and improve my overall health rather than waste time on less important things. Space 20

EXAMPLE 6

Consider a person who is used to having 1 to 2 brown bowel movements per day that are easily passed. Now the person has only one hard texture bowel movement every several days and strains to pass it. There is abdominal discomfort and frequent bloating. This dialogue is an example of how using the device facilitates analysis and consequent action based upon understanding the biopsychological aspects of the person's overall health.

Proctor: What problems are you having?

Patient: I used to have one or two regular bowel movements each day. Now I only have a hard stool every several days. I also have more severe pain in my abdomen and more frequent bloating. These symptoms are worrying me. Space 1

Proctor: Have any other things been going on in your life since these symptoms began? Space 13

Patient: Recently my life seems to be going more and more out of control. Just thinking about everyday tasks makes me feel anxious. Space 13

Proctor: These different gastrointestinal symptoms you are experiencing may be related to each other. Before exploring this more, you should first undergo some diagnostic tests to find out information about the possible causes of these symptoms. Space 14

(At this time the interview is suspended for a period of time while tests are done. The interviewer and person reconvene later).

Proctor: It is good news that the tests do not show any diseases such as endocrine, thyroid, or tumor blockage—for example, a colorectal mass—causing your constipation, abdominal pain, or bloating. Space 4

Proctor: But there still may be other causes of your gastrointestinal symptoms these diagnostic tests cannot reveal. Let's take this opportunity to focus in greater detail on recent events going on in your life. Space 15

Patient: This year both of my children both started new schools. One entered middle school and the other entered high school. Since they are in school all day, I decided to begin working outside the home half time. Twenty hours a week did not seem like a lot of time when I first started, but in a short period of time, my house has become more dirty, messy and disorganized. Even my children seem much sloppier in their habits and home routine. My job has also turned out to be more high-pressured than I expected, and I work a very irregular schedule. Space 15

Proctor: Did symptoms like the constipation, pain and bloating begin around the time you started the new job? Perhaps emotions are also affecting you physically by creating a vicious cycle of anxious feelings. This anxiety can interfere with your ability to function well at home and at work—defeating efforts to improve your life. Space 16

Proctor: You have had constipation before. In the past, we treated the constipation with several different types of bulk laxatives. You had softer stools, but persistent abdominal discomfort and bothersome bloating. You probably need to do more than merely change diet and daily fluid intake. Space 7

Proctor: To improve your anxious feelings without medication, try learning progressive relaxation techniques, for example, using special visualization exercises. You can also decrease anxiety by engaging in regular physical activity. Space 17

Proctor: To briefly sum up, your symptoms may best respond to more than just dietary changes, increased fluid intake, and laxatives. It seems there is a strong psychological influence on these gastrointestinal symptoms. Progressive relaxation and visualization techniques can help decrease anxiety and also improve your abdominal discomfort and bloating. Space 18

Patient: I need to change many of my current habits. I still do not drink enough fluids each day. In fact, I often do not eat meals regularly. I need to stick to a daily routine of regularly scheduled, balanced meals and at least five glasses of liquid a day. I must also start taking the bulk laxative at a regular time each morning, otherwise I often forget to take it. Space 10

Patient: I think that regular exercise would relieve my anxiety. It would be convenient to take a walk several times each week before picking up my children from afternoon activities. I am intrigued by the idea of progressive relaxation techniques; I will inquire about a local instructor to teach these to me. Space 19

Patient: Relief of these gastrointestinal symptoms will help me to perform better at my job. Then perhaps I can get a transfer or promotion to a different department with work hours that better accommodate the balanced lifestyle we are discussing. Space 20

EXAMPLE 7

Consider a person who has suffered a hip fracture, undergone a total hip replacement, and made good progress in rehabilitation. The person is now experiencing depression that is causing physical decline. This is an example of a clinical dialogue between the person's adult child and a proctor that illustrates the way in which the device facilitates understanding the biopsychological aspects of the person's overall health.

Adult child: My mother suffered a hip fracture, and the orthopedic surgeon performed a total hip replacement surgery. Mother initially had successful rehabilitation and returned to her independent life at home. Things were returning to normal until about a month ago when she started becoming much less physically active. Space 1

Adult child: Now when I ask her about any of the activities she always liked, mother does not seem interested. Although she looks tired, she says she does not sleep well. We went to her favorite restaurant, but mother barely ate a thing. She does not say much when I am with her. Mother only talks about how much her back and stomach ache, but she does not appear to be in pain. I'm concerned because recently she has been saying that life does not seem worth living anymore. Space 13

Proctor: The decline you describe is not characteristic of the physical problems related to recovery from a hip fracture. There may be a link between her physical problems and her emotional state; in fact, her emotions can accentuate any pain she may experience. Space 14

Adult child: I have tried to be sure that no other medical problems are occurring. At the six-week postoperative evaluation, mother's surgeon thought that her condition was very good. She had very little pain at that visit. I have taken mother back for physical therapy visits twice since then. The physical therapist was equally impressed with mother's successful recovery. Mother's annual medical evaluation by the family physician took place recently. The physician prescribed over-the-counter anti-inflammatory medicine that relieved the occasional minor aches until about one month ago when mother started to decline. Space 4

Proctor: Your mother's signs and symptoms are characteristic of clinical depression—insomnia, poor appetite, no pleasure in activities, feelings of life not worth living, and complaints of diffuse pains. Space 15

Proctor: Her emotional state can interfere with her physical function. If her activity level greatly decreases, your mother may become even more weak and deconditioned. Her irregular appetite can lead to overall poor nutrition. Space 16

Proctor: Until her depression is effectively treated, there is little benefit to simply pushing her to do more. The treatment needs to start with an effective antidepressant medication. Here is a prescription for medication she should take once daily. Space 7

Proctor: You may want to find out more information about the special exercise program at the local community center. This program costs very little and it is conveniently located nearby. Even if your mother does not feel like participating yet, sign her up now for the next session. Hopefully by that time, her depression will improve and she will feel like participating in the activities. Space 17

Proctor: The most effective approach to improving your mother's condition requires antidepressant medication and family support. Counseling can also help increase her insight and her resolve to get better. I will recommend several different therapists; all are very capable, but your mother may relate better to one personality than to another. Space 18

Adult child: Since mother is reluctant to take new medication, I will set up a pillbox to make sure the antidepressant medicine is easily available and taken correctly. I will also have one of the family members stop by her house every 2 days to make sure she takes the medicine as prescribed and to see if she is having any side effects. Having family members visit may also help lift her spirits. Space 10

Adult child: I will call the therapists' offices now to find out more about an initial visit for mother. I will also call the community center about the exercise programs for seniors. Even if I cannot push mother to be more active now, at least I'll be prepared when she gets better in the future. Space 19

Adult child: It is clear that my mother's full recuperation did not just end with a successful hip replacement surgery or the rehabilitation. Depression can undo all of the gains of this past year and threaten mother's independence. To effectively help her, I need to carefully watch that she maintains good nutrition and gets the right treatment. I also need to help her get connected with an activity program to rebuild her strength. By paying attention to all of these factors, I can help her accomplish a lot more than just taking the medicine prescribed. Space 20

As evidenced by the above examples, the device and method of the present invention provide for a dialogue to address the physical, social/environmental, and psychological problems of any person. All three types of analysis can occur synergistically to improving a person's overall well-being by applying biopsychosocial analysis. The invention permits professionals and non-professionals to recognize factors (such as anxiety, depression, illness beliefs, and feelings about care, etc.) that perpetuate illness. It also allows people to limit and to control such factors that perpetuate illness by improving stress management skills, social support, and preventive health measures. All this is accomplished without a script—sometimes via interaction with a trained proctor—allowing the person to address all his/her concerns. It further provides a more certain way to address all three domains of health. One embodiment of the invention uses a colorful hemiannular device that people can use and keep to remind them of how to apply biopsychosocial analysis to their health issues. Alternatively, it or a copy of it may be kept with the person's records to inform a health care professional more broadly about the person's concerns and motivations. The method does not significantly increase the cost of an office visit to a professional, and certainly has the potential of significantly reducing all costs of treatment by recognizing and controlling factors which perpetuate illness and result in repeat visits for the same physical symptoms.

It will be appreciated by those of skill in the art that the factors represented by the first, third, and fifth sections of the apparatus are interchangeable. It is possible, for example, for the first, third and fifth sections to be representative of psychological, physical and social/environmental factors, respectively. In other words, the first, second, and third factors of the analysis are representative of any number of variables from the group of social, environmental, physical, biological, and psychological variables.

It will also be appreciated that the apparatus and method of the present invention may be used for analysis other than that of biopsychosocial analysis. As discussed herein, the apparatus and method may also be used for analysis of the interrelationship between intellectual and non-intellectual capital of an organization.

Examples 8, 9, 10, and 11 below illustrate the use of the apparatus in the method of the present for analysis of business factors. In these examples, the first section may represent employee relationships, customer relationships, and organization relationships. The third section may represent employee motivation and behavior and organization motivation and behavior. The fifth section may represent physical capital, financial capital, employee knowledge and skills, and organization structure and processes. Collectively, the factors are those that comprise the total market value of an organization. Stated another way, the first factor is representative of relational variables including but not limited to relationships of more than one entity; the second factor is representative of psychological variables including but not limited to motivations and behaviors; and the third factor is representative of other capital assets of at least one entity. Here, the term entity refers to persons or other organizations that are related to or involved in the organization being analyzed.

EXAMPLE 8

Consider the example of two different medical centers whose boards of directors want to merge their organizations in order to achieve economies of scale and greater market share. In exploring this venture, it becomes increasingly apparent that merging backroom operations like billing and scheduling is easier than joining very different groups of physicians into cooperative entities. Ultimately the merger feasibility analysis concludes that linkages must evolve separately for each different specialty area.

There are deep divisions between cardiology groups at the two medical centers because one is much more academically (i.e., teaching/research) oriented than the other. A clinical (C1, C2) and administrative (A1, A2) representative from each of the two different cardiology groups meet with a neutral leader (L) present to explore whether a merger can occur within the cardiology specialty area.

L: What is the problem?

A1: This merger has been fraught with almost unbelievable problems. The two cardiology groups have not established any relationship at all. The physicians rarely even talk to each other. (yellow—indicative of problem with relationship or interaction)

A2: Even more surprising is the depth of animosity between the two groups. (blue—indicative of problem with motivation, behavior, or emotion)

L: This mutual avoidance and these angry feelings detract from our desired goal of improving the health care delivery process. (green—establishing linkage between yellow problem and blue problem)

A2: Cardiologists in the academic group never interact with those in the community group because they have no reason to do so. There have been no overlapping activities. (yellow—indicative of cause for yellow problem)

A1: The cardiology groups consist of members with deeply held beliefs that influence their perspective. The academic group believes teaching and research are the most important considerations while the community cardiologists believe that patient care comes above all other considerations. (blue—indicative of cause for blue problem)

L: It is artificial to separate teaching, research, and patient care. There are fundamental links between these areas; everyone—cardiologists, patients and the program—would benefit from developing these units further. (green—establishing linkage between yellow cause and blue cause)

L: To do that we need a physician representative from each cardiology group with clear authority to speak for the other members. These representatives need to meet on a regular basis. (yellow—indicative of solution to yellow cause)

L: These will need to be physicians who are broad-minded enough to understand different points of view. Above all, each will need to believe that clinical practice, clinical research, and teaching can all combine together in a way that strengthens the operation of the entire cardiology program. (blue—indicative of solution to blue cause)

C1: Perhaps we should seek an academic cardiologist heavily involved in clinical practice and a community physician who has had exposure to research and new treatments in the past. Physicians with such experiences would be best suited to begin developing a balanced model of clinical practice, clinical research and teaching. Although balanced cardiology programs like this exist in other cities, there are none in this area. (green—establishing linkage between yellow solution and blue solution)

L: Let's present the goal that way. Now what would it take to get each group to appoint a new representative? Can all of you here develop stronger relationships among yourselves and aid in this endeavor? (yellow—indicative of change needed for yellow solution)

C2: Let's start feeling out each cardiologist's background: to see whether the physician has had a positive research experience during his or her career including training at a medical center with a balanced clinical, research, teaching program. (blue—indicative of change needed for blue solution)

L: Meanwhile, I will identify model programs and contact the program directors for further information and relevant background materials. This can be a very valuable resource when the representatives finally get together. (green—establishing linkage between change needed for yellow solution and change needed for blue solution)

EXAMPLE 9

A company has recently had large layoffs. Management's communications to employees and the public about the layoffs have essentially had a matter-of-fact "we had to do this" message. But the company's previously excellent product quality has begun to deteriorate to unacceptable levels. Even though the company's cost structure is now average within its industry, decreasing sales because of poor product reliability threaten the company's survival.

Manager 1: According to every outcome measure we track, our product quality is worse than it has ever been. This threatens the future of the company. Space 1

Manager 2: The situation is even worse than you think because employee morale is very low. Many staff members have been operating in an almost paralyzed manner since the layoffs. I've never seen this degree of emotional tumult here before. Space 13

Manager 1: We have been telling the employees for a long time that we had to cut the workforce to lower our costs and be competitive. Isn't it enough to be honest with them? After all, at some companies managers tell lies to the employees and later hand out pink slips. Space 14

Manager 1: Our product quality is declining because people are not refocused on their work and on our product. Our new organizational chart is clear. Everyone knows his or her place within the reporting structure. Space 4

Manager 2: You need to understand that employee morale is low because people are grieving over the loss of the company they cherished. Right after the layoffs, some employees were in denial but now many have gone beyond denial to the point where they are feeling very angry. Space 15

Manager 2: The cause of the quality problem is our failure to refocus the employees' anger and channel some of their emotional energy to more productive work. Space 16

Manager 1: We can do this by showing how layoffs for some employees have been necessary to allow us to pay those who are left working here. There is a place and a salary for everybody left. Besides, employees should remember that we did not cut their benefits as much as we could have. Space 7

Manager 2: The employees' grieving process over their loss is much more complex than that. Little by little, individual employees will see beyond their anger.

Some will eventually go through a process of forgiving themselves, the company, and us. But some may continue to harbor depressed feelings that can affect them for a long time to come. Space 17

Manager 2: By focusing more of the attention of the human resources department to deal with these emotional issues, we will be able to help individual employees and the company as a whole to move forward. Space 18

Manager 1: We will certainly need to budget additional money and perhaps even hire more staff for the human resources department. We may also need funds for outside consulting services in the near future to deal with all of this effectively. Space 10

Manager 2: I will find out more about how my colleagues at other companies feel. In the past, people I know have hired consulting firms that offer supportive psychological services for employees of downsized companies. Let me ask questions about their experiences with these consulting firms. Space 19

Manager 1: Looking back, it now seems that most of our exhortations to employees about getting back to work, putting the past behind, and looking toward the future have fallen largely on deaf ears. As managers, we can more effectively move forward by first working through the complex lingering emotional issues in our company. Space 20

EXAMPLE 10

Consider a specialized education publishing company whose customers are primarily government agencies and school systems. A marketing strategy of advertising and direct sales has produced good growth for several years, but sales are now starting to decline. For the first time, the company recently hired sales representatives. But their efforts have not increased the amount of business as anticipated. Despite greater quality and quantity of advertising and greater expenditure on the sales force, the company still is not meeting growth targets.

Executive 1: Our company is failing to meet growth targets because of poor sales. What is happening? Space 1

Executive 2: Most of the new salespeople have good background experience and interpersonal skills. This is not the problem. Space 2

Executive 2: In fact, I am told that despite declining sales, current customers find our sales representatives helpful and personable. But a piece of this puzzle must be missing, and we need to figure out what it is. Space 3

Executive 1: Our company's customer retention is good. We have wide geographic distribution, and we continue to supply the same share of existing customer business. But our company desperately needs new customers. Space 4

Executive 2: The sales representatives are focusing nearly all of their efforts on strengthening and maintaining existing relationships. Our priority has been to keep the business of our current customer base. Space 5

Executive 1: That is not good enough. The sales representatives' skills must be enhanced and redirected so they can develop new customer relationships, increase sales, and make us grow. Space 6

Executive 1: We need to do whatever is necessary. One place to start is re-examining whether our current product lines need to be changed. Space 7

Executive 2: Rather than changing the product line, we may do best to start by increasing the number of sales calls to new potential customers. Several of our long established customers are key national officers in large and important governmental and educational organizations made up of their colleagues. Perhaps these key customers who are already satisfied with our company can help direct and introduce us to new prospective customers. Space 8

Executive 1: The answer is attention to both the product line and to new accounts. Perhaps the key customers you just mentioned would provide leads and tell us about how they would like to see the product line changed. Space 9

Executive 1: I will evaluate the feasibility of redirecting the sales representatives' focus from their current customer responsibilities. This can free their time to call on new accounts. If not, we may need to find the resources to hire more sales people. Space 10

Executive 2: The current sales representatives need to be given information about which of their current customers have national organizational ties. We can work with the sales people to decide how to develop a close relationship with these organizations. Space 11

Executive 1: We must include an entirely different schedule, budget, manpower plan, and approach to our salespeople this year to make all that you and I have just been discussing a reality. Space 12

EXAMPLE 11

An employee (E) has always had excellent attention to detail. The employee has worked quickly and efficiently. The person has consistently met deadlines and remembered instructions well. The person has also had very good interaction with others and with the supervisor. Over the past two months, the quality and quantity of the employee's work has declined noticeably. The supervisor has recommended the employee meet with an Employee Assistance Program staff member (S) to look further into why this is happening. At the first meeting, the two use this device to analyze the situation.

S: In recent weeks, your supervisor is increasingly concerned that you are forgetting instructions and need much more extensive directions than before. You are taking much more frequent breaks and you seem much less adaptable to changes in work procedures. Space 1

S: Coworkers sense that you seem much more sensitive to criticism than ever before—the supervisor reports that you get irritable very easily, almost as soon as anyone says something to you. It often appears to others as if you are trying to build a wall around yourself. Space 2

S: I do not understand what is affecting your declining performance at work and deteriorating interactions with others. Because you have been well liked and conscientious at work for so many years, you probably want to figure out what something is causing this marked change. Space 3

S: Are you feeling any differently now than you have before? Space 13

The employee writes down her feelings that have gradually become more severe over the past several months: Space 13

E:
No interest.
Not motivated
No energy

Can't get to sleep
Can't concentrate at home or work
Have let almost everybody down
What is the use of it all? Space 13

S: These feelings must be having an effect on your work. I encourage you to consult a physician to look into this further. Space 14

(The interview is suspended for a period of time while the employee goes for a physician visit. The physician makes a diagnosis of clinical depression that the employee shares with the Employee Assistance Program staff member when the two reconvene later.)

E: The physician says that I have clinical depression, and that this is a fairly common condition. Space 15

E: I was totally unaware of how directly and pervasively the depression has been affecting my work. Space 4

S: If depression has caused you to lose motivation and interest in things going on around you, your work can suffer as a consequence. Because of poor concentration, you may become distracted very easily and take more frequent breaks. Your low energy level can accentuate these problems. Space 16

E: But why does depression make me treat people at work in a hostile manner? Space 5

S: Clinical depression can affect your whole demeanor. Sleeping poorly at night can make you more irritable during the day. With little interest and low motivation, your attempts at teamwork on the job can suffer. Because you feel so pessimistic and guilty, you may sometimes even wonder why anyone would want to work with you. Space 6

E: I have just started treatment with an antidepressant medicine. My physician strongly urged counseling and recommended several different professional therapists. Space 17

S: There are ways to change the expectations of your job to make your workday more comfortable. But for these adjustments to happen, you may need to share information about the depression with your supervisor. By following through and changing your approach to tasks at work, you can help ensure greater success in your job. Space 7

E: I have many concerns about how the antidepressant medicine can affect my work. It may take weeks to produce a positive effect. Even then, the medicine may produce bothersome side effects that can interfere with my activities. Space 18

S: Your coworkers can be a source of emotional support and encouragement. But right now they may not understand your feelings or your condition. In fact, some may mistakenly think that you purposely want to distance yourself from them. Space 8

S: It will help you to feel accepted as part of a team. Decreasing your feelings of loneliness will improve your depression and effectiveness at work. Space 9

E: I want to be very conscious of how I feel and whether I think the antidepressant medicine is working. To avoid missing any doses, I need to make a habit of taking the medicine at the same time every day. I still must choose the therapist best suited for my needs from among the recommendations my physician made. Space 19

E: I will ask my supervisor to describe in a very straightforward way what tasks and activities I need to do each day. The supervisor also needs to write out very clear guidelines for me about the new changes in the work procedures. Space 10

E: I will do best on the job with consistency in my assignments over the next few weeks. Now that I am more aware of my condition, I also need some flexibility regarding pace of work and break times. I will let my physician know immediately about problems with the antidepressant medicine. Space 20

E: I want to share information about my condition and what has been happening with certain coworkers. But I will have to carefully select people with whom I am most comfortable. Space 11

E: And before I make a decision to tell coworkers about my depression, I need to find out how the supervisor plans to assign work. It will be absolutely essential to work with a team in order to accomplish some of these tasks. Such strained relationships with coworkers have made it virtually impossible for me to participate in certain very important work. Now I am ready to start changing that. Space 12

It will be appreciated by those of skill in the art that use of the apparatus and method of the present invention has application to the business world. An organization can more accurately analyze its total market value by addressing hidden capital inherent in the relationships, motivation and behavior of employees, customers, and organizations. Use of the apparatus can also help organizations identify these different forms of intellectual capital and how they affect the more commonly recognized physical, financial, and structural forms of capital.

It will also be appreciated that, as in the application to biopsychosocial analysis, the order of the factors represented in this business analysis are interchangeable.

Figure 4:
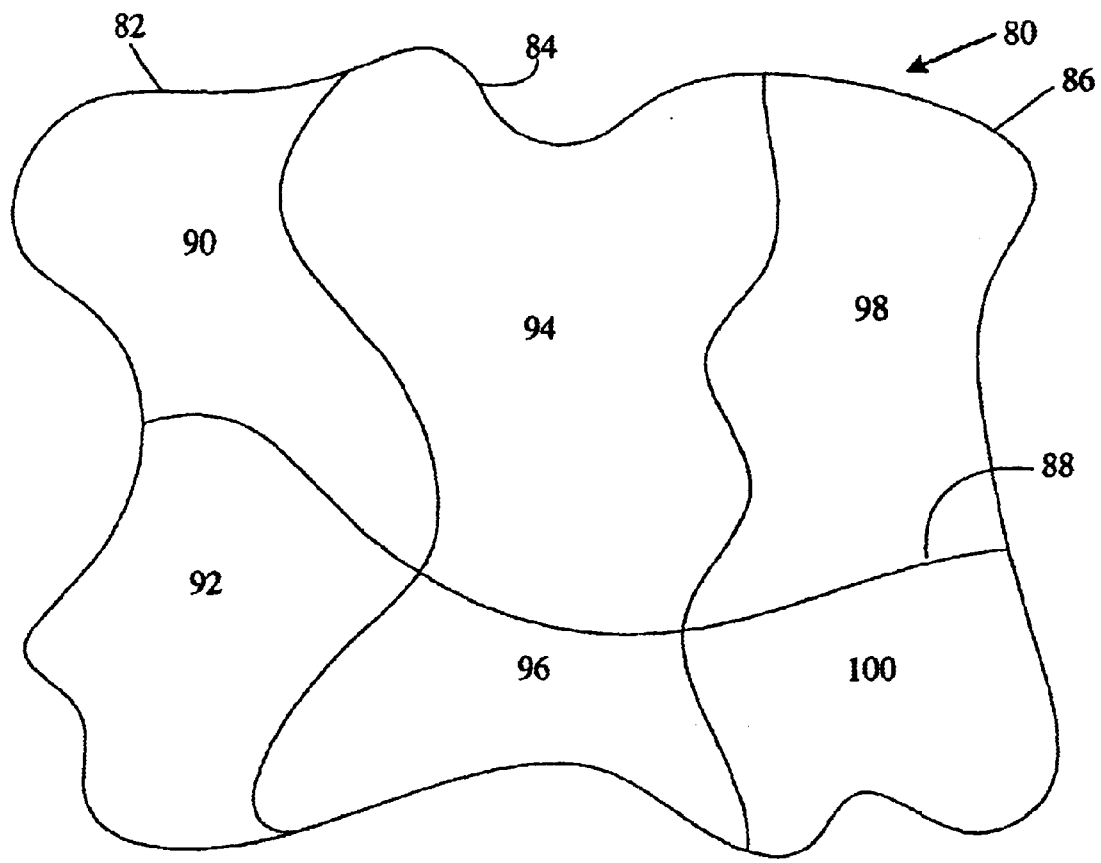
FIG. 4 shows a front view of a second embodiment of the apparatus according to the present invention.

Referring now to FIG. 4, there is shown a second embodiment of the apparatus of the present invention used for analysis involving a first factor and a second factor, wherein the first and second factors are related as expressed by a first relationship. In this embodiment, base 80 is divided into first section 82 representative of the first factor of the analysis, second section 84 representative of the first relationship, and third section 86 representative of the second factor. Base 80 is further divided by line 88 into first and second subsections. The first subsection comprises spaces 90, 94 and 98, and the second subsection comprises spaces 92, 96, and 100. The first subsection is indicative of a symptom, event, experience, problem, or causal relation, and the second subsection is indicative of a solution, treatment, needed change, or adjustment.

The embodiment of FIG. 4 simplifies the analysis by reducing the number of subsections to be considered. Such simplification may be desired for an individual who may have difficulty with more detailed analysis or who is unwilling to spend a great deal of time on the analysis.

Figure 5:
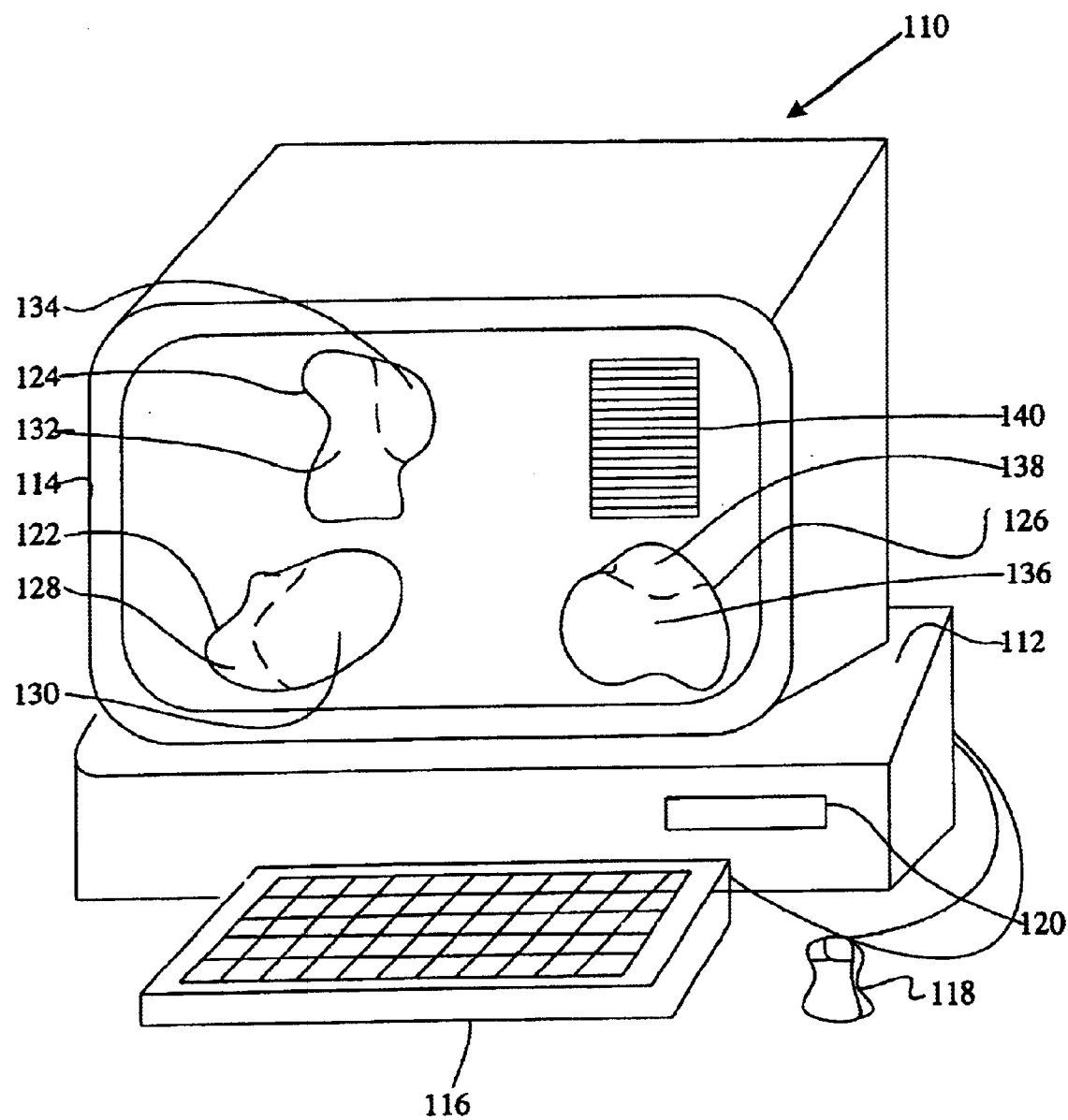
FIG. 5 shows a perspective view of a third embodiment of the apparatus according to the present invention.

Referring now to FIG. 5, there is shown a third embodiment of the apparatus of the present invention. In this embodiment the user interacts with computer 110 to perform analysis involving a first and second factor and a first relationship between the first and second factors. Computer 110 includes processing unit 112, visual display means 114, keyboard 116, and mouse 118; and media recorder 120, such as a disk reader or CD-ROM reader. A software means for presentation of the graphics and text described below is loaded by media reader 120 for execution by processing unit 112, as is well known in the art. The software means displays first graphical area 122 representative of the first factor of the analysis, second graphical area 124 representative of the first relationship, and a third graphical area 126 representative of the second factor. Each of the graphical areas 122, 124, and 126 comprises first subsections 128, 132, and 136, respectively, and second subsections 130, 134, and 138, respectively. Each first subsection 128, 132 and 136 is indicative of a symptom, event, experience, problem, or causal relation. Each of the second subsections 130, 134, and 138 is indicative of a solution, treatment, needed change, or adjustment.

The software means also is capable of displaying prompts 140 on visual display means 114 to interact with the user for posing questions related to the first and second factors. The user may enter responses via keyboard 116 and/or mouse 118 by means well known in the art. It is possible that graphical and/or textual and/or color markers indicative of the user's responses can be placed on the appropriate subsections of graphical areas 122, 124, and 126 by means well known in the art.

It will be appreciated by those of skill in the art that the means for prompting or interacting with the user may comprise prompts as illustrated in FIG. 5, or may comprise other communication mechanisms, such as voice or sound projection, as is well known in the art. It will also be appreciated that various types of processing units, visual display means, and input devices may be used to create an electronic embodiment of the invention for execution of the method of the present invention.

Figure 6:
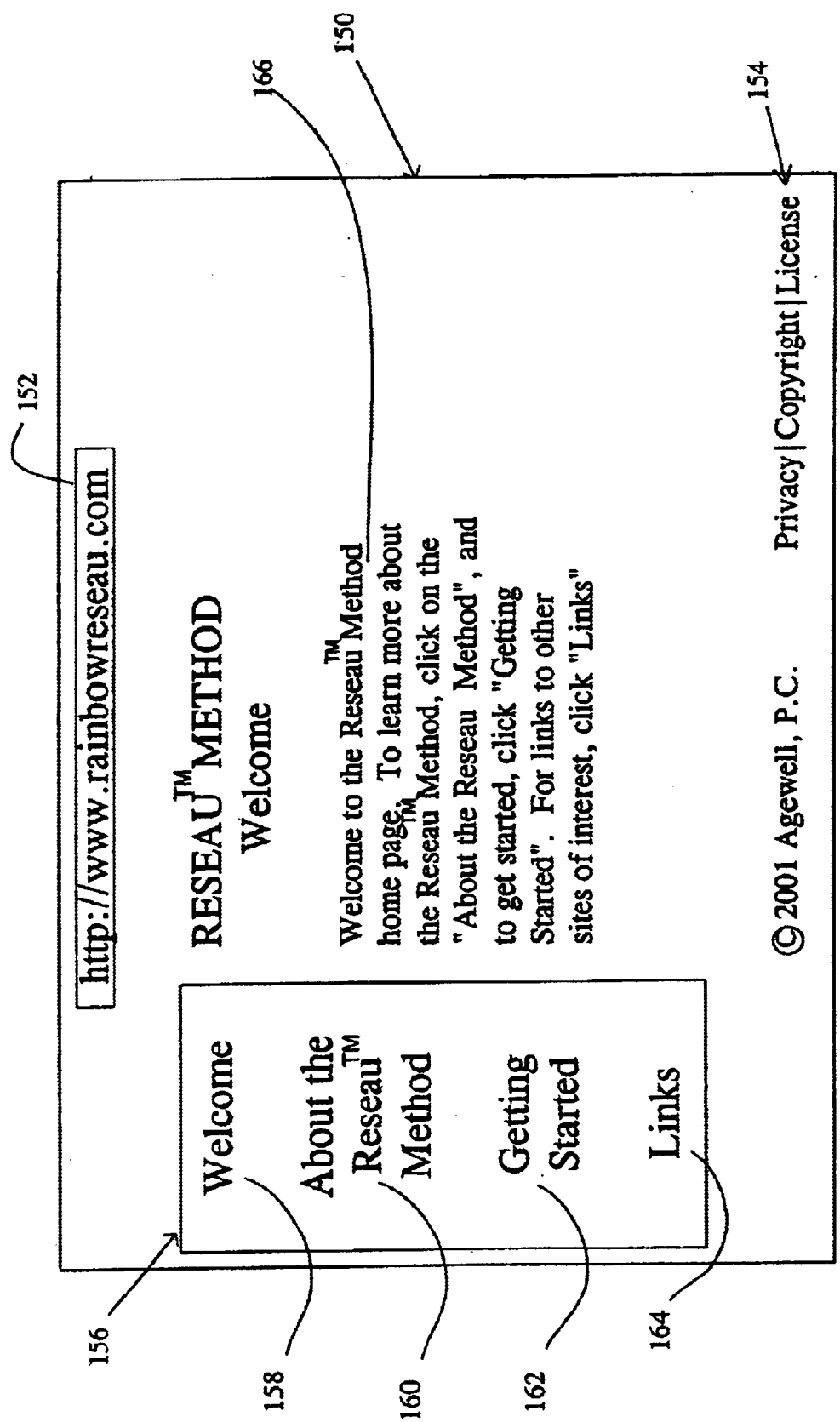
FIG. 6 shows an exemplary screen printout of a welcome page according to one embodiment of the present invention.

Referring now to FIG. 6, there is shown an exemplary screen printout of a welcome screen according to one embodiment of the present invention. Welcome screen 150 may be displayed on visual display means 114 of computer 110 by control of software residing on computer 110. Alternately, welcome screen 150 may be displayed through network connection to other computer(s) and/or processor (s). Consider, for example, operation of browser software such as Microsoft Corporation's Internet Explorer™ or Netscape Corp.'s Netscape™ for connection to the global computer network known as the Internet. In such instance, the software running the analysis tool resides on a server or computer connected to the Internet as is well known in the art. It is this latter configuration used as the example set forth in FIGS. 6, 7, and 8.

Returning now to FIG. 6, welcome screen 150 includes website designator 152 indicating the location of the software running the analysis tool software of the present invention. In this instance, website designator 152 shows that the website is "www.rainbowreseau.com". Welcome screen 150 also includes footer 154 showing the copyright designation "©2001 Agewell, P.C." and providing links to the sites privacy statement, copyright policy, and license terms and conditions as is well known in the art.

Welcome screen 150 also includes side bar 156 for high-level negotiation through the website www.rainbowreseau.com. In this embodiment, side bar 156 contains links to the websites welcome content by Welcome menu option 158, to general information about the analysis tool known here as the Reseau™ Method by About the Reseau™ Method menu option 160, to instructions and execution of the analysis tool by Getting Started menu option 162, and links to other sites (as is well known in the art) by Links menu option 164.

Located in the center of welcome screen 150 is welcome content 166 providing the user with general information about the analysis tool and high-level navigation through the website.

Figure 7:
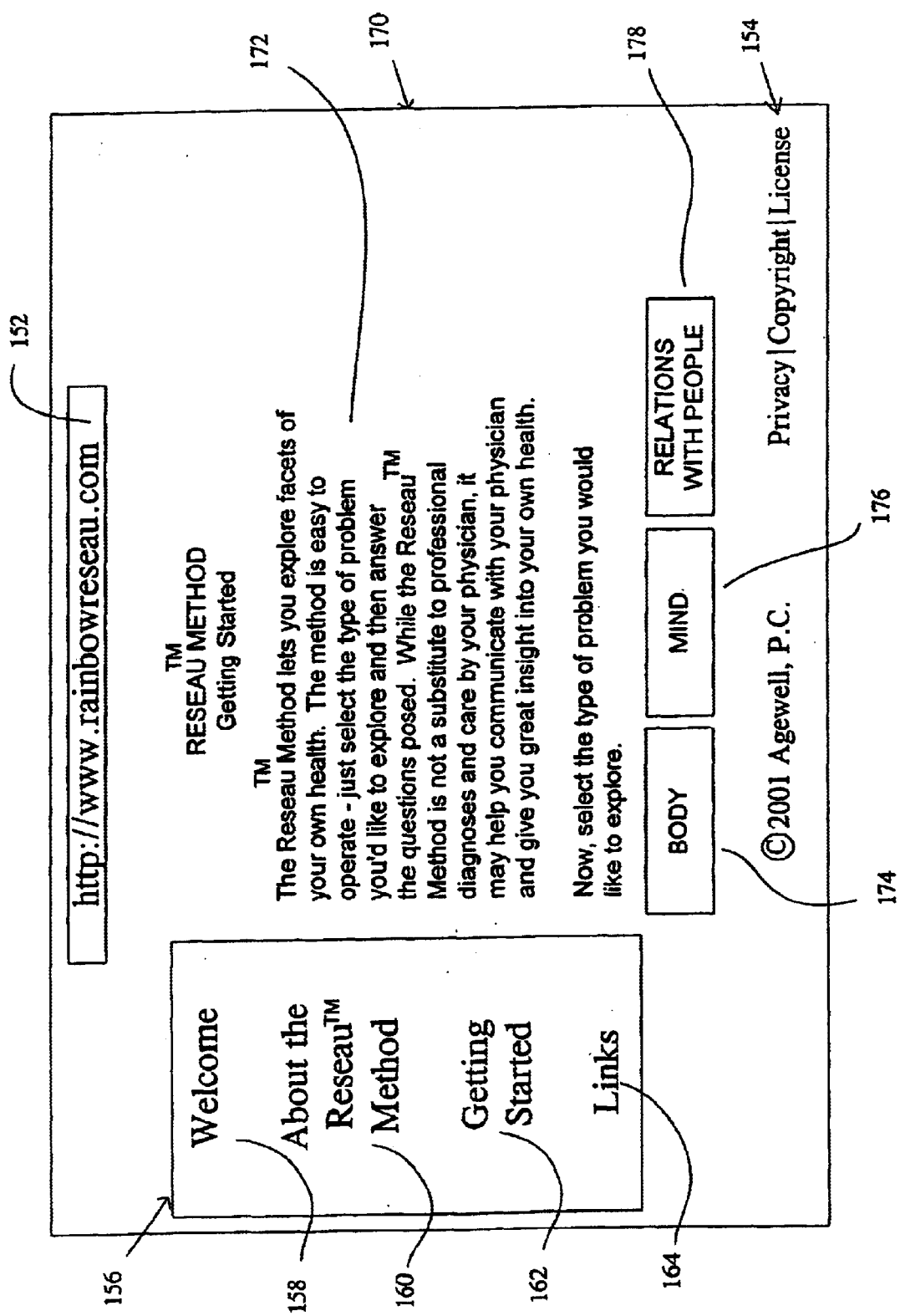
FIG. 7 shows an exemplary screen printout of an informational page according to one embodiment of the present invention.

If the user selects (by means well known in the art) Getting Started menu option 162, informational screen 170 of FIG. 7 is displayed at computer 110. Information screen 170 includes much of the same features as welcome screen 150, but differs significantly in content. Informational content 172 gives general information about the Reseau™ Method and general instructions. Informational content 172 is directed toward the biopsychosocial analysis in this instance. Information content 172 would be different if used for the business analysis described hereinabove.

To begin analysis using the Reseau™ Method, the user selects body button 174, mind button 176, or relations with people button 178. Body button 174 is indicative of a biological problem. Mind button 176 is indicative of a psychological problem, and relations with people button 178 is indicative of a social problem. If the Reseau™ Method were used for business analysis, these buttons 174, 176, and 178 would be replaced with buttons indicative of relationships, motivations/behavior, and capital assets.

Figure 8:
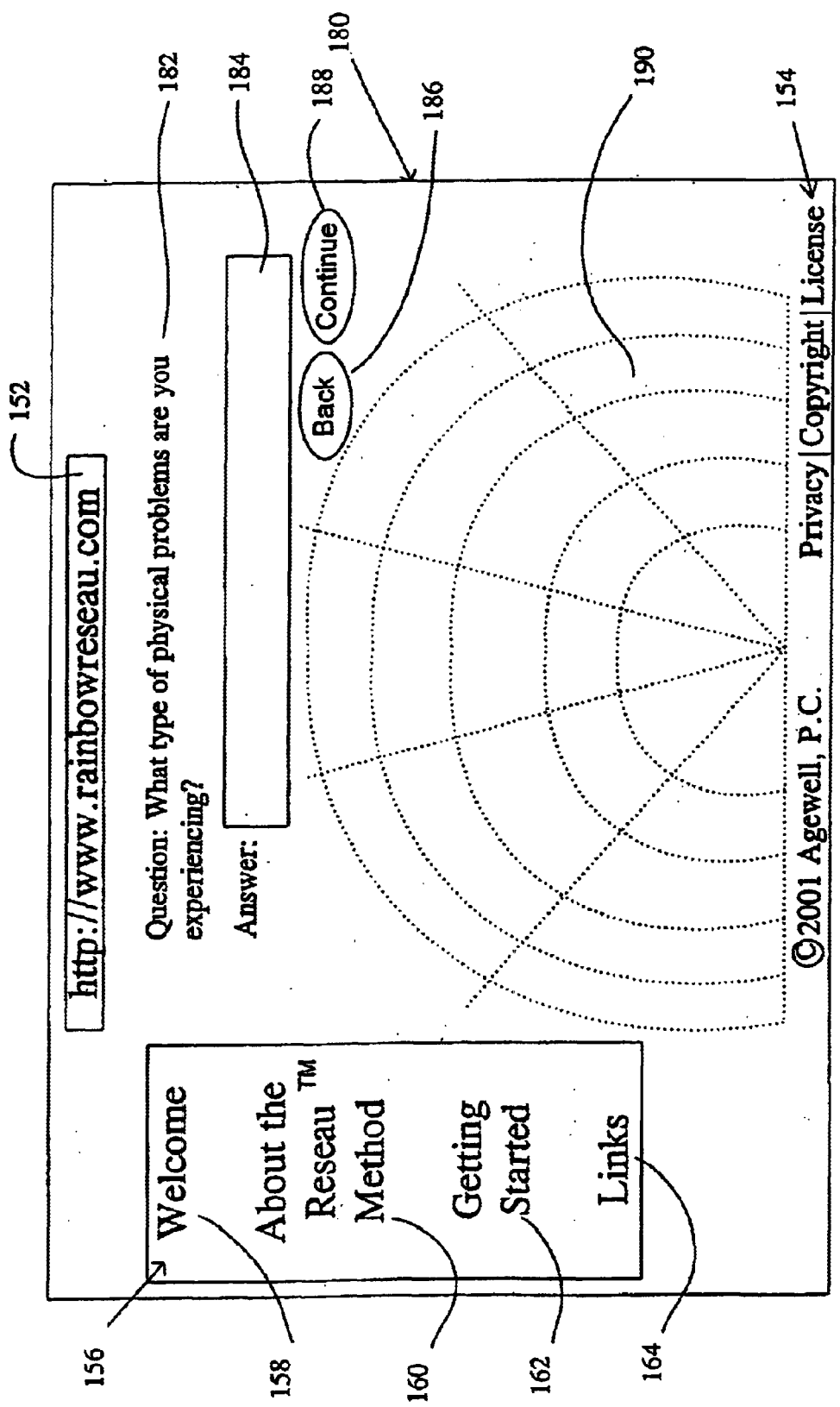
FIG. 8 shows an exemplary screen printout of an interactive page according to one embodiment of the present invention.

If, at FIG. 7, the user selects body button 174, the exemplary interactive screen 180 of FIG. 8 is displayed. Interactive screen 184 includes website designator 152, footer 154, and side bar 156 as found in the screens of FIGS. 6 and 7. Interactive screen 180 also includes question space 182, answer space 184, back button 186, continue button 188, and graphic image 190.

Question space 182 is for posing questions to a user. Answer space 184 is a space for a user to input an answer to the question posed in question space 182. Back button 186 allows the user to go back to the previously displayed screen. Continue button 188 allows the user to advance to the next screen. Graphic image 190 is, in this embodiment, an outline of the device as shown in FIG. 2. Graphic image 190 is filled in as the user responds to questions in the manner described hereinabove.

Because graphic image 190 is displayed electronically, certain liberties may be taken to enhance the display. For example, as a user completes answers, the colors may be shaded into each other to result in a more aesthetically pleasing display. Further, when answering questions in rings 50, 52, 54, and 56, a space may be further divided into a series of slices to reflect a series of questions related to the subject matter covered in that slice. Multiple questions may be particularly helpful when exploring inner rings 50 and 52, but could be used on any ring and in any space.

It will be appreciated by those of skill in the art that the question and answers may be dealt with in this electronic version by means other than visual display and keyboard entry. For example, answers may be posed by a playing an audio file which the browser or a plug-in to the browser can comprehend. Further, the user may answer questions or instruct screen movement (back, continue) by speech recognized by the browser. Such alternate display and entry means are contemplated to be within the scope of the invention.

The operation of the embodiment of FIGS. 6, 7, and 8 will now be explained by way of example. In response to the question "What type of physical problem are you experiencing?" posed in question space 182 of interactive screen 180, the user answers; "I have been having urinary problems. I am incontinent." in answer space 184. This response causes space 1 of graphic image 190 to appear (in color, sound, voice, symbol, word, etc.) The system would then refresh question space 182 and answer space 184 and display in question space 182 the inquiry, "How does that make you feel?" The user might answer in answer space 184, "It makes me feel lonely and ashamed." This response causes space 13 of graphic image 190 to appear.

At this point, question and answer spaces 182 and 184 are again refreshed, and question space 182 is filled with a question about the frequency or severity of the problem. By the user completing an answer to this question, space 14 of graphic image 190 would appear to indicate the possibility of a link between the key trigger word(s) of space 1 ("urinary" and/or "incontinent") and the key trigger word(s) of space 3 ("lonely" and/or ashamed).

Space 4 of graphic image 190 would then appear with possible causes of the user's symptoms, events, or experiences expressed in space 1 of graphic image 190. Space 15 of graphic image 190 would then appear with a display, sound, voice, word, color, etc. of possible causes of the respondent's symptom(s), event(s), or experience(s) expressed in space 13. This process is continued in a manner akin to the previous examples given hereinabove.

It will be appreciated by those of skill in the art that the questions posed and suggestions given in response to the user's input involve the use of relational database(s) and decision tree(s) as is well known in the art. The present invention involved the use of such technology to provide the artificial intelligence required to utilize electronic means rather than a trained proctor or health care provider to ask questions, listen to the answers, and make appropriate suggestions. Accordingly, the electronic method and device, like the other embodiments, described herein, can proceed in a varied sequence accompanied by screen display, live voice, and/or voice simulation in the spaces in addition to posting of words, colors, and symbols.

It will also be appreciated by those of skill in the art that the posting of suggestions may, in the embodiment, involve linking to other resources. Alternatively, the user may select Links menu option 164 to seek such other resources. Such resources may include a physician, home health agencies, products, (hot pack, vitamins, adult diapers, etc) for which information is available on the Internet. In this manner, the user may seek appropriate assistance and/or products to address the suggestions made by the system.

It will be further appreciated that the user system need not comprise a personal computer. Other devices capable of bidirectional communication over a network are contemplated to be within the scope of the invention. Such devices may include a laptop computer, a personal data assistant, a Palm™ Pilot, a telephone, or similar device.

It will be still further appreciated that the network of the present invention may be comprised of one or more bidirectional communication networks. Such networks include, but are not limited to, intranet, extranet, local area network, wide are a network, satellite communication, telephone lines, fiber optic networks, and the Internet.

It will be appreciated by those of skill in the art that the apparatus and method of the present invention can be used for a period for applications involving two or more factors in which at least two of the factors are related. The factors represented may, for example, be two of the three factors discussed above for biopsychosocial analysis or relational/motivational-behavioral/physical-financial-structural analysis of an organization.

It will also be appreciated that the color code of the apparatus of the present invention represents unique and distinctive domains of information. Not only is the color scheme unique, it differs from the natural color spectrum. Further, although each color employed is associated with a particular domain of information (e.g., red is associated with physical information), the colors of the device can be placed in different areas of the device. For example, blue or yellow could be placed in the center (72–108 degrees) of the device rather than red. Green could be used as a background color for areas outside the areas of the concentric rings. Still, the color scheme is not a requirement of the bases to be within the scope of the invention.

It will also be appreciated that the device of the present invention may be used without the support means shown in FIG. 1. The base may be made by any myriad of means well known in the art based on the functionality described herein.

It will be further appreciated that the method of the present invention permits for flexibility in the order and time-frame that domain analysis and interactions proceed. Note, for example, that Examples 1 and 2 herein illustrate such flexibility as to the order of domains analyzed, and the order of treatment indicators discussed with the patent. Further, Example 2 illustrates a break in time (for the purpose of diagnosis) in the method of the present invention.

It will be still further appreciated that the method of the present invention does not require interaction between more than one individual. An individual alone could use the apparatus and method by questioning himself/herself, or if the individual is given some form of instruction and is able to understand those instructions, or if the individual receives prompts or instructions in an electronic form as discussed herein. Thus, as used in the claims, the term "interaction" may relate to a monologue, to conversation between or more persons, or to the provision of instructions and/or prompts such as in written form or in electronic form.

The term "divided" as used in the claims is meant to indicate no specific requirement of division of the sections of apparatus or of the size or location of the resulting sections. The sections may or may not be contiguous as illustrated in FIGS. 1 and 4 or separated as illustrated in FIG. 5. The sections may be of similar size and shape, or may vary with regard to size and/or shape. Likewise, the term "subdivided" as used in the claims does not indicate a particular shape or size requirement for the resulting subsections.

It will also be appreciated that sections representing a relationship between two factors of the analysis need not be positioned between the two related factors as shown in FIGS. 2, 4, and 5. Nonetheless, such positioning may be desired so that the position of the represented relationship is adjacent each of the represented related factors.

It will be yet further appreciated that the apparatus and method of the present invention may be used for analysis of any of the domains, either individually or in any combination. Further, the apparatus and method have application in healthcare and in non-health care analysis. For example, the apparatus and method may be used for employee relations and/or human resource purposes in a corporation.

I claim:

1. A system for analysis involving a first factor and a second factor, wherein the first and second factors are related as expressed by a first relationship, the system comprising:
    a software system;
    a network capable of bidirectional communication; the network operably connected to the software system;
    a user system operable connected to the network such that the software system and user system may communicate bidirectionally, the user system including output means for asking one or more questions of a user operating the user system, an input means to allow the user to respond to the one or more questions, and a visual display means; and
    a software means residing on the software system and/or the user system, alone or in combination, the software means operable to output on the output means the one or more questions and to input with the input means responses to the one or more questions, the software means further operable to display on the visual display means first, second, and third graphical areas, the first graphical area representative of the first factor, the second graphical area representative of the first relationship, and the third graphical area representative of the second factor, each of the first, second, and third graphical areas further divided into first and second subsections, each of the first subsections indicative of a symptom, event, experience, problem or causal relation, and each of the second subsections indicative of a solution, treatment, needed change or adjustment.

2. The system of claim 1, wherein the software system comprises a server, the network comprises the Internet, and the user system comprises a computer.

3. The system of claim 2, wherein the software means comprises a first software program residing on the software system and a browser residing on the user system.

4. A method for analysis of a first factor and a second factor, wherein the first and second factors are related as expressed by a first relationship, the method comprising the steps of:
   a. providing a system of analysis, the system comprising:
      a software system;
      a network capable of bidirectional communication; the network operably connected to the software system;
      a user system operable connected to the network such that the software system and user system may communicate bidirectionally, the user system including output means for asking one or more questions of a user operating the user system, an input means to allow the user to respond to the one or more questions, and a visual display means; and
      a software means residing on the software system and/or the user system, alone or in combination, the software means operable to output on the output means the one or more questions and to input with the input means responses to the one or more questions, the software means further operable to display on the visual display means first, second, and third graphical areas, the first graphical area representative of the first factor, the second graphical area representative of the first relationship, and the third graphical area representative of the second factor, each of the first, second, and third graphical areas further divided into first and second subsections, each of the first subsections indicative of a symptom, event, experience, problem or causal relation, and each of the second subsections indicative of a solution, treatment, needed change o'r adjustment; and
   b. posing at least one question to the user with the output means.

5. The method of claim 4, further comprising the step of:
responding to the at least one question with at least one answer with the input means.

6. The method of claim 5, further comprising the step of:
displaying on the visual display means a response indicative of the at least one answer.

* * * * *